US010275889B2

(12) United States Patent
Chen et al.

(10) Patent No.: US 10,275,889 B2
(45) Date of Patent: Apr. 30, 2019

(54) IMAGE PROCESSING APPARATUS, MAGNETIC RESONANCE IMAGING APPARATUS AND IMAGE PROCESSING METHOD

(71) Applicant: Toshiba Medical Systems Corporation, Otawara-shi (JP)

(72) Inventors: Yu Chen, Beijing (CN); Cui Xu, Beijing (CN)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/678,214

(22) Filed: Aug. 16, 2017

(65) Prior Publication Data

US 2018/0053306 A1    Feb. 22, 2018

(30) Foreign Application Priority Data

Aug. 17, 2016    (CN) .......................... 2016 1 0680717
Aug. 1, 2017    (JP) ................................ 2017-149289

(51) Int. Cl.

| G06T 7/136 | (2017.01) |
| A61B 6/03 | (2006.01) |
| A61B 6/00 | (2006.01) |
| G06T 7/00 | (2017.01) |
| G06T 7/11 | (2017.01) |

(52) U.S. Cl.
CPC .............. *G06T 7/136* (2017.01); *A61B 6/032* (2013.01); *A61B 6/5217* (2013.01); *G06T 7/0012* (2013.01); *G06T 7/11* (2017.01); *G06T 2207/10081* (2013.01); *G06T 2207/10088* (2013.01); *G06T 2207/20101* (2013.01); *G06T 2207/30061* (2013.01)

(58) Field of Classification Search
CPC ................... G06T 7/136; G06T 7/0012; G06T 2207/20101; G06T 2207/10081; A61B 6/032; A61B 6/5217
USPC ........................................................ 382/131
See application file for complete search history.

(56) References Cited

U.S. PATENT DOCUMENTS 9,042,620 B2 *    5/2015    Kohlberger .......... G06K 9/6209
382/131

FOREIGN PATENT DOCUMENTS

| CN | 102243759 A | 11/2011 | |
| CN | 102243759 B * | 5/2014 | ............... G06T 7/00 |

OTHER PUBLICATIONS

Chunming Li, et al. "Distance Regularized Level Set Evolution and Its Application to Image Segmentation", IEEE Transactions on image processing, 2010, vol. 19, No. 12, 12 pages.*

* cited by examiner

*Primary Examiner* — Gregory F Cunningham
(74) *Attorney, Agent, or Firm* — Oblon, McClelland, Maier & Neustadt, L.L.P.

(57) ABSTRACT

An image processing apparatus according to an embodiment includes processing circuitry. The processing circuitry recognizes at least one of chest wall, vessels, nodules, and tumors by increasing sensitivity to a gradient and a sensitivity to a cavity structure in three-dimensional data including a lung area. The processing circuitry generates lung image data corresponding to the lung area by performing a data removing process for removing data derived from the chest wall and a data holding process for holding data derived from at least one of the vessels, the nodules, and the tumors on a basis of a result obtained by the recognizing. The processing circuitry outputs the lung image data.

11 Claims, 7 Drawing Sheets

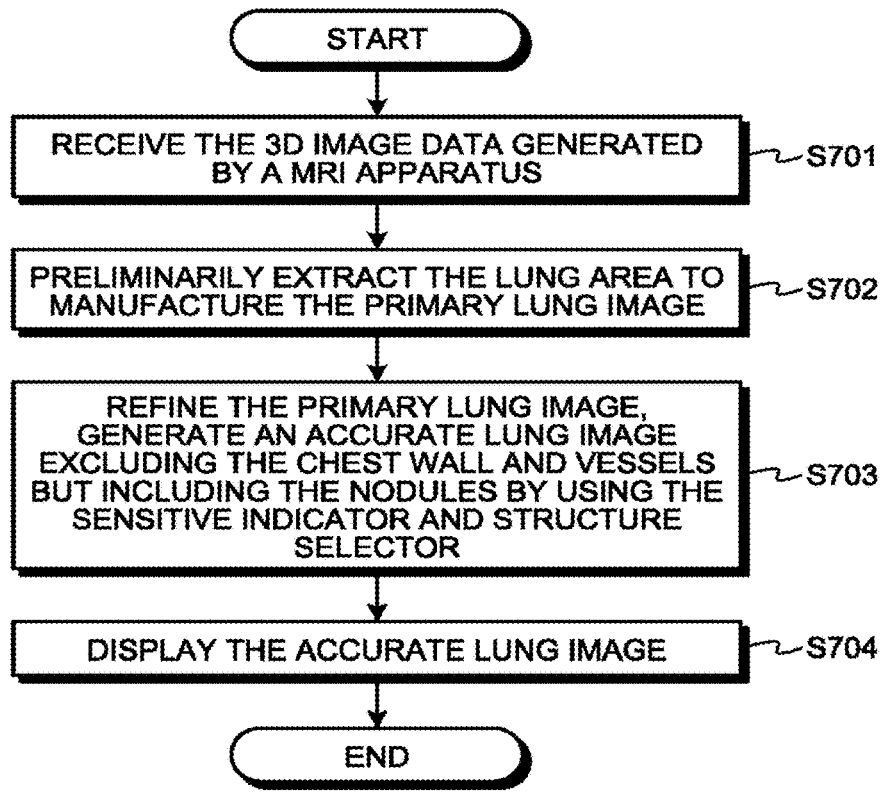
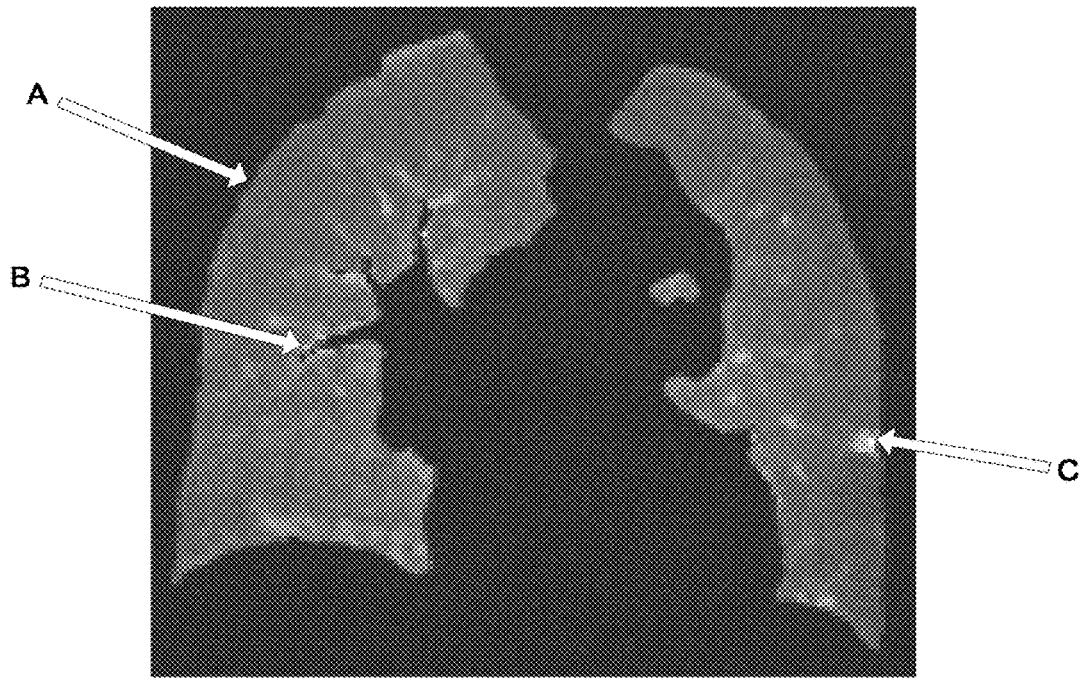

FIG.9
(1)
(2)
(3)
FIG.10
(1)
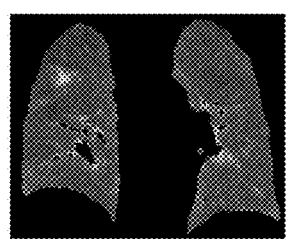
(2)
(3)

FIG.11
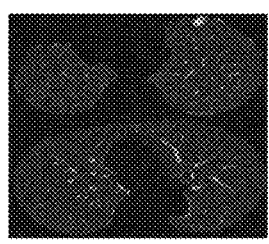 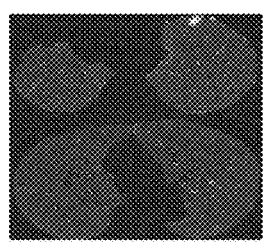 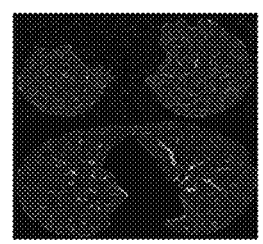
(1) (2) (3)
FIG.12
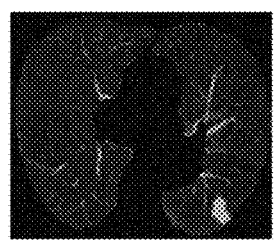 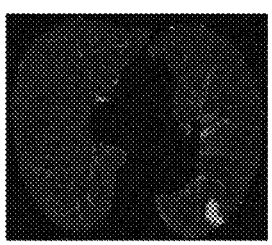 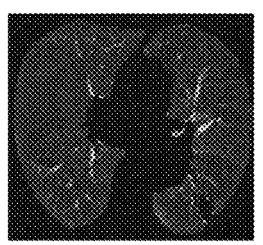
(1) (2) (3)

IMAGE PROCESSING APPARATUS, MAGNETIC RESONANCE IMAGING APPARATUS AND IMAGE PROCESSING METHOD

CROSS-REFERENCE TO RELATED APPLICATIONS

This application is based upon and claims the benefit of priority from Chinese Patent Application No. 201610680717.4, filed on Aug. 17, 2016, and Japanese Patent Application No. 2017-149289, filed on Aug. 1, 2017; the entire contents of which are incorporated herein by reference.

FIELD

Embodiments described herein relate generally to an image processing apparatus, a magnetic resonance imaging apparatus and an image processing method.

BACKGROUND

In recent years, as the development of the image recognition technology, the segmentation technology for segmenting the organs from the medical images has attracted more and more attention. For example, lung segmentation plays an important role in visualization and quantitative analysis of lung parenchyma. Moreover, 3D lung segmentation technology and lung vessel excluding technology are of great significance for accelerating the diagnosis procedure.

In the prior art, generally the images acquired by CT (computerized Tomography) are employed for lung segmentation, since MRI (Magnetic Resonance Imaging) apparatus is unsuitable for depicting the lung, but more suitable for the head. At present, the are many techniques for CR images based lung segmentation and lung vessel extraction.

For example, patent document 1 (U.S. Pat. No. 9,042,620) discloses a method for multi-organ segmentation and a lung segmentation for three-dimensional CT images, wherein marginal space learning method is used to generate initialized mesh for level set, and level set is used to get a distance map based accurate segmentation.

Patent document 2 (CN102243759B) discloses a geometric deformation model based three-dimensional lung vessel image segmentation method, wherein level set function is used to segment lung vessel for high-resolution and high-contrast CT images.

However, the segmentation methods of patent document 1 and patent document 2 are not suitable for the images acquired by MRI apparatus. For MRI apparatus, it is difficult to perform accurate 3D lung segmentation and lung vessel excluding with existing technology.

For example, the non-patent document 1 ("Distance Regularized Level Set Evolution and Its Application to image Segmentation [J], Chunming Li, Chenyuang Xu etc., IEEE Transactions on Image Processing") discloses a method applicable to lung segmentation.

In lung segmentation of medical images, a commonly used method is: firstly inputting the image data acquired by a medical image acquisition apparatus; performing preliminary lung segmentation using the rough segmentation methods such as threshold method or binarization segmentation method on the basis of the image data to extract the lung image; and then refining the preliminary segmentation results to obtain more accurate segmentation results.

However, the existing segmentation technique is not sensitive to the low contrast areas on boundaries between the lung parenchyma and the chest wall, and is ineffective in the processing of cavity structure (such as vessels and nodule/tumor).

FIG. 13 is an exemplary figure representing the results of the existing lung segmentation processing for the chest image acquired by MRI apparatus. As shown in FIG. 13, the data of chest wall tissue is still left in the area of the extracted lung image pointed by arrow A after refining. On the other hand, the thin vessels could be included, but the relatively thick vessels cannot be correctly included, as shown in the area pointed by arrow B, meanwhile, the nodules area as pointed by arrow C cannot be included as well.

BRIEF DESCRIPTION OF THE DRAWINGS

FIG. 7 is a flow chart representing the lung segmentation processing according to the second embodiment of the present invention;

FIG. 8 is an exemplary figure representing the results of the lung segmentation processing according to the second embodiment of the present invention;

FIG. 9 is an exemplary figure representing different processing result generated based on different selections of the structure selector when process the image data of MRI apparatus;

FIG. 10 is another exemplary figure representing different processing results generated based on different selections of the structure selector when process the image data of MRI apparatus;

FIG. 11 is an exemplary figure representing different processing results generated based on different selections of the structure selector when process the image data of CT apparatus;

FIG. 12 is another exemplary figure representing different processing results generated based on different selections of the structure selector when process the image data of CT apparatus;

DETAILED DESCRIPTION

Figure 1:
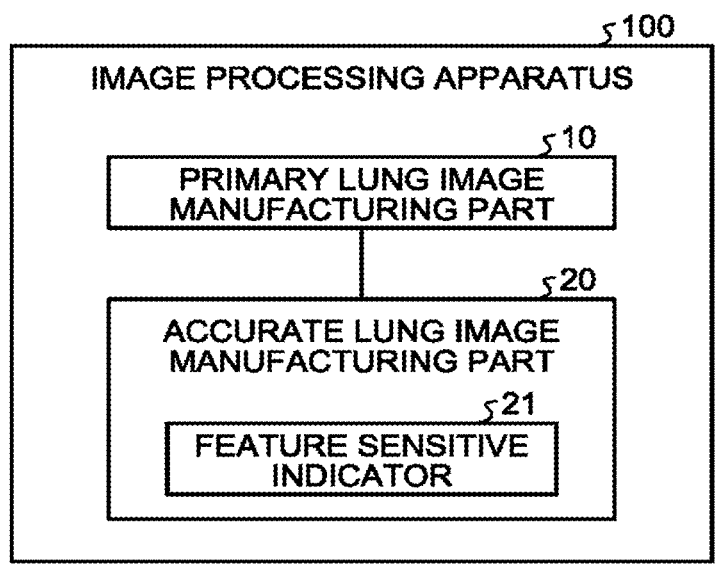
FIG. 1 is a block diagram representing an image processing apparatus according to the first embodiment of the present invention.

The present invention is provided for solving the above problems, the purpose is to provide an image processing apparatus and an image processing method for performing a more accurate lung segmentation processing.

One technical solution of the present invention is an image processing apparatus for extracting the lung area in an image acquired by an image acquisition apparatus, comprising: a primary lung image manufacturing mechanism for extracting the lung area from the image data including the lung to manufacture a primary lung image; and an accurate lung image manufacturing mechanism for processing the primary lung image based on the image data to manufacture an accurate lung image; wherein the accurate lung image manufacturing mechanism comprises a feature sensitivity indicating unit, the feature sensitivity indicating unit uses the sensitivity to gradient and the sensitivity to cavity structure for processing, such that the accurate lung image excludes the chest walls and includes the cavity structures.

Furthermore, another technical solution o the present invention is an image processing method for extracting the lung area in an image acquired by an image acquisition apparatus, comprising: a primary lung image manufacturing step to extract the lung area from the image data including the lung to manufacture a primary lung image; and an accurate lung image manufacturing step to process the primary lung image based on the image data to manufacture an accurate lung image; wherein in the accurate lung image manufacturing step, the sensitivity to gradient and sensitivity to cavity structure are used for processing, such that the accurate lung image excludes the chest walls and includes the cavity structures.

According to the present invention, a more accurate lung segmentation could be performed such that the lung area can be more accurately segmented from the medical image. Particularly, by use of the sensitivity to gradient and sensitivity to cavity structure in conjunction, the chest wall area and the cavity structure area in the image could be distinguished more sensitively, so that chest walls are excluded better and the cavity structures are retained based on this distinguishing.

Moreover, in the image processing apparatus of the present invention, the accurate lung image preparation mechanism may also comprise a selecting unit which performs a selection processing such that the cavity structures are selectively excluded from the accurate lung image.

According to the present invention, for example, we can select to excludes the vessels from but includes the nodules in the segmentation result by enabling the pixel of vessels or the pixel of nodules not to be reflected in the sensitivity to cavity structure, thereby the vessels and nodules can be better distinguished so as to be processed respectively. Because of the optional and more reliable vessel excluding, it is optional for the users whether or not to exclude the vessels, and the vessels could be excluded while the nodules are retained, therefore the efficiency in reading photographs is improved.

In addition, the present invention is particularly effective for processing of the lung image of the MRI apparatus. The result of the MRI apparatus has positive effect on the diagnosis of the diffusion of lung cancer, but the MRI apparatus is seldom used for the acquisition of lung due to a clear MR signals of lung is difficult to obtained. By applying the present invention to the MRI apparatus, the accuracy of the whole lung segmentation of the MRI apparatus can be improved, and the lung mask can be generated in cardiac and aortic analysis.

The present invention relates to an image processing apparatus for processing images, which could be realized by executing software having various functions of the image processing apparatus thorough devices having CPU (Central Process Unit), such as an separated computer, connected to the image acquisition apparatuses, such as X ray apparatus, or may be realized in form of hardware by serving as the circuits that can execute various functions of the image processing apparatus. Moreover, the image processing apparatus of the present invention may also be pre-mounted on the above-mentioned medical image acquisition apparatus as a part of the medical image acquisition apparatus such as CT apparatus or magnetic resonance imaging apparatus etc.

In the following, reference is made to the drawings for illustrating the preferable embodiments of the present invention. In the various embodiments, the image acquisition apparatus is preferably the MRI apparatus, and the present invention is preferably used for the lung segmentation processing of the medical image data acquired by MRI apparatus. But it is also applicable to the lung segmentation processing for other medical image acquisition apparatuses such as CT apparatus and ultrasonic wave apparatus.

In addition, illustration is made in following embodiments by adopting the acquired image data as the three-dimensional image data, however, the present invention is also applicable to image processing in other dimension such as two dimension. Furthermore, in the exemplary figures used in the present invention, for purpose of a more clear illustration, certain cross-section in the three-dimensional image is used for illustrating.

Additionally, in different embodiments, same reference signs are used for the same component, and the repeated explications are omitted properly.

First Embodiment

FIG. 1 is a block diagram representing an image processing apparatus according to the first embodiment of the present invention. As shown in FIG. 1, image processing apparatus 100 comprises at least a primary lung image manufacturing part 10 and an accurate lung image manufacturing part 20.

The primary lung image manufacturing part 10 receives the three-dimensional image data of the chest acquired by the MRI apparatus, extracts the lung area from the received image data by rough segmentation methods such as threshold method or binarization segmentation method, so as to manufacture the primary lung image. The primary image manufacturing part 10 may be circuits or software modules which are capable of realizing the above functions. In other words, the three-dimensional image data is MRI image data acquired by the MRI apparatus. The primary image manufacturing part 10 serving as a pre-processing part manufactures pre-processed lung image data which is obtained by extracting a lung area from the three-dimensional image data through pre-processing different from a data removing process an a data holding process.

Figure 2:
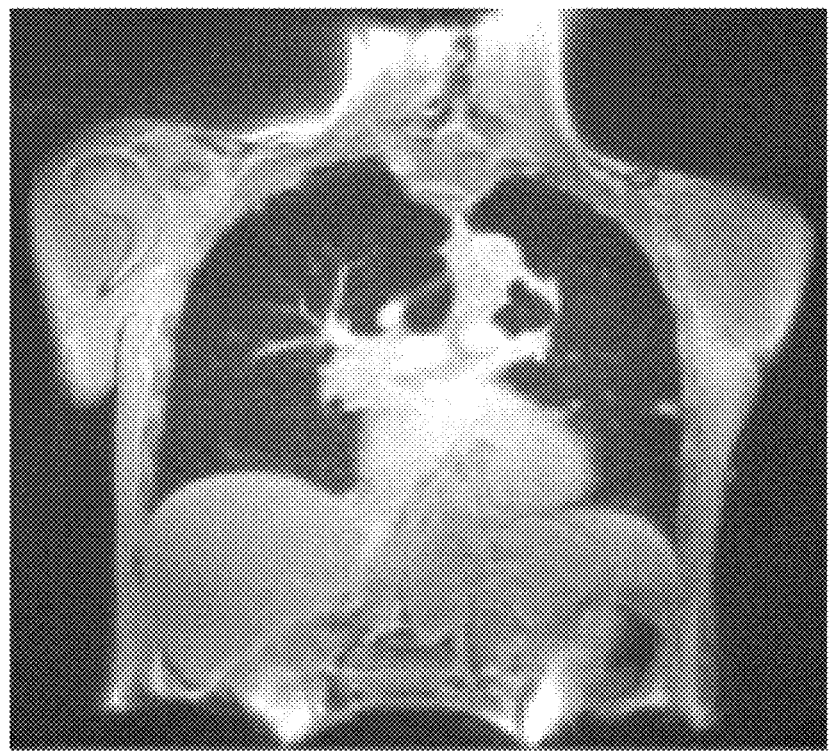
FIG. 2 is an exemplary figure representing the chest image acquired by MRI apparatus.
Figure 3:
FIG. 3 is an exemplary figure representing the primary lung image.

FIG. 2 is an exemplary figure representing the chest image acquired by MRI apparatus. FIG. 3 is an exemplary figure representing the primary lung image. The primary lung image manufacturing part 10 extracts the lung area from the three-dimensional image data as shown in FIG. 2 to form the primary lung image as shown in FIG. 3. In the primary lung image, typically only the pixels of lung parenchyma having common characteristics are extracted, so it is difficult to show the existence of the substance contained in the lung such as vessels, and the edges processing is roughness.

The organs or tissues different from the lung parenchyma such as vessels, nodules and tumors etc., are collectively referred to as "cavity structure" herein.

The accurate lung image manufacturing part 20 further processes the primary lung image, modifying the primary lung image according to the three-dimensional image date of the MRI apparatus and thereby manufacturing accurate lung image. The accurate lung image manufacturing part 20 may be circuits or software modules which are capable of realizing said functions.

For example, by using the level set constructed by the pixels of primary lung image as the initial level set, in combination with the original image data information such as the three-dimensional image data of the MRI apparatus, level set evolution segmentation is performed, the accurate lung image is obtained by such iterative algorithm. Such partial differential equation that can reflect the level set evolution and includes the level set function is set as a level set function model.

Herein, the accurate lung image manufacturing part 20 further modifies the primary lung image by taking the level set function model as the accurate processing model for the lung segmentation, forming the accurate lung image that the edge area is more finely processed and that is desirable to contain cavity structure except for the vessels.

In order to complete the above goal, in the first embodiment, the accurate lung image manufacturing part 20 comprises a feature sensitivity indicator 21 which utilizes the sensitivity to gradient and sensitivity to cavity structure for processing, such that the accurate lung image generated by the accurate lung image manufacturing part 20 does not include the chest wall, but include the cavity structure. In other words, the feature sensitivity indicator 21 serving as a recognizing part recognizes at least one of the chest wall, the vessels, the nodules, and the tumors by increasing the sensitivity to the gradient and the sensitivity to the cavity structure in the three-dimensional data including the lung image. On the basis of the result obtained by the recognizing part, the second image manufacturing part 20 serving as a generating part performs the data removing process for removing data derived from the chest wall and the data holding process for holding data derived from at least one of the vessels, the nodules, and the tumors. These processes are performed to generate lung image data corresponding to the lung area. The second image manufacturing part 20 serving as the generating part performs the data removing process and the data holding process on the pre-processed lung image data manufactured by the pre-processing part, thereby manufacturing the lung image data.

Specifically, the feature sensitivity indicator 21 comprises a gradient sensitivity indicator g sensitive to the gradient of the original image data and a cavity structure sensitivity indicator sign(k)k sensitive to the cavity structure of the initial image data, wherein the gradient sensitivity indicator g can be represented by following formula (1):

$$g = e^{-m*I*|\nabla G \oplus I|^2} \quad (1)$$

In formula (1), I is the grey value matrix of 3D image of the original image data, $\nabla G$ is the derivative of the Gaussian kernel, and m is the coefficient set arbitrarily as needed.

By setting the gradient sensitivity indicator g as the form of index of Exp, it has such a relation with the image grey that the descent speed of g increases as the grey value I increasing. Particularly, as compared with the existing gradient, sensitivity indicator, the value of g in the first embodiment is smaller in case that the grey values I are the same, so the descent speed of the value of g becomes higher as the grey value I increasing. In short, the gradient sensitivity indicator g can be represented by a function (exponential function) including a grey value I as an exponent. In other words, the function, (gradient sensitivity indicator g) including the grey value as an exponent can be used by the feature sensitivity indicator 21 serving as the recognizing part to represent sensitivity to the gradient. With such use of function, data derived from the chest wall can be recognized.

As such, using art exponential function like formula (1) as a gradient sensitivity indicator g can accelerate gradient descent, such that more sensitive to the gradient. Thus, substituting such sensitivity indicator into, for example, the accurate processing model of lung segmentation based on level set function φ enables the generated accurate lung image to exclude the chest wall.

In addition, in the cavity structure sensitivity indicator sign(k)k, $$k = \text{div}\left(\frac{\nabla \phi}{|\nabla \phi|}\right)$$

is mean curvature value, and sign(k) satisfies formula (2):

$$\text{sign}(k) = \begin{cases} 0, & k \geq \lambda \\ 1, & k < \lambda \end{cases} \quad (2)$$

wherein λ is the coefficient set arbitrarily as needed.

The cavity structure sensitivity indicator sign(k)k is sensitive to the cavity structure, so the cavity structures such as vessels, nodules and tumors etc. can be monitored by adding the cavity structure sensitivity indicator sign(k)k to the accurate processing model. In short, the cavity structure sensitivity indicator sign(k)k is a function for outputting "0" or "1" in accordance with the result obtained by comparing a curvature value (mean curvature value) and a threshold λ. In other words, binarization of the curvature value obtained by comparison with the threshold can be used by the feature sensitivity indicator 21 serving as the recognizing part to represent sensitivity to the cavity structure. With such use of binarization, data derived from the vessels, the nodules, and the tumors can be recognized.

In the first embodiment, the feature sensitivity indicator 21 strengthens the diffusion energy of the cavity structure in the accurate processing models by obtaining the difference between the gradient sensitivity indictor g and the cavity structure sensitivity indicator sign(k)k, such that the accurate lung image processed by the accurate processing model contains the vessels and nodules. I other words, the feature sensitivity indicator 21 serving as the recognizing part allows multiplying level set distance regularization by a value obtained through subtraction of the sensitivity to the cavity structure from the sensitivity to the gradient. With such multiplication, the cavity structure can be included in the lung image data.

For example, when illustration is made by means of the level set distance regularization based accurate processing model represented in following formula (3) as adopted in the prior art, the feature sensitivity indicator 21 combines the gradient sensitivity indicator g and the cavity structure sensitivity indicator sign(k)k with formula (3), particularly replaces the original gradient function of formula (3) with the gradient sensitivity indicator g of formula (1) of the present invention, so that the accurate lung image manufacturing part 20 employs the accurate processing model of lung segmentation based on level set distance regularization as shown in formula (4) to process the primary lung image.

$$\frac{\partial \phi}{\partial t} = \mu \mathrm{div}(d_p(|\nabla \phi|)\nabla \phi) + \lambda \delta_\varepsilon(\phi)\mathrm{div}\left(g\frac{\nabla \phi}{|\nabla \phi|}\right) + a\delta_\varepsilon(\phi) \quad (3)$$

$$\frac{\partial \phi}{\partial t} = \mu \mathrm{div}(d_p(|\nabla \phi|)\nabla \phi) + \lambda \delta_\varepsilon(\phi)\mathrm{div}\left(g\frac{\nabla \phi}{|\nabla \phi|}\right) + a\delta_\varepsilon(\phi)(g - \mathrm{sign}(k)k) \quad (4)$$

wherein, with regard to formula (3), it is well known that Φ is a level set function, ∂ is partial derivative, ∇ is gradient, div is divergence, |...| is absolute value representing length of vector, and μ, λ, α, ε are corresponding coefficients. In addition, with regard to the function $$d_p(s) = \frac{p'(s)}{s},$$

please refer to the recordation of existing literature such as the above-mentioned non-patent document 1.

Figure 4:
FIG 4. is an exemplary figure representing the results of the lung segmentation processing according to the first embodiment of the present invention.

FIG. 4 is an exemplary figure representing the results of the lung segmentation processing according to the first embodiment of the present invention. By modifying the primary lung image shown in FIG. 3 using the accurate processing model of formula (4), the accurate lung image shown in FIG. 4 can be obtained.

As shown in FIG. 4, There is no data of the chest wall tissue left in the edge area pointed by arrow A due to the acceleration effect of the gradient sensitivity indicator g. Besides, under the simultaneous effect of the cavity structure sensitivity indicator sign(k)k, the cavity structures shown by arrows B and C such as the vascular tissues and nodules sire completely retained.

In the first embodiment, the primary lung image manufacturing part 10 corresponds to "primary lung image manufacturing mechanism", the accurate lung image manufacturing part 20 corresponds to "accurate lung image manufacturing mechanism" and the feature sensitivity indicator 21 corresponds to "feature sensitivity indicating unit".

Figure 5:
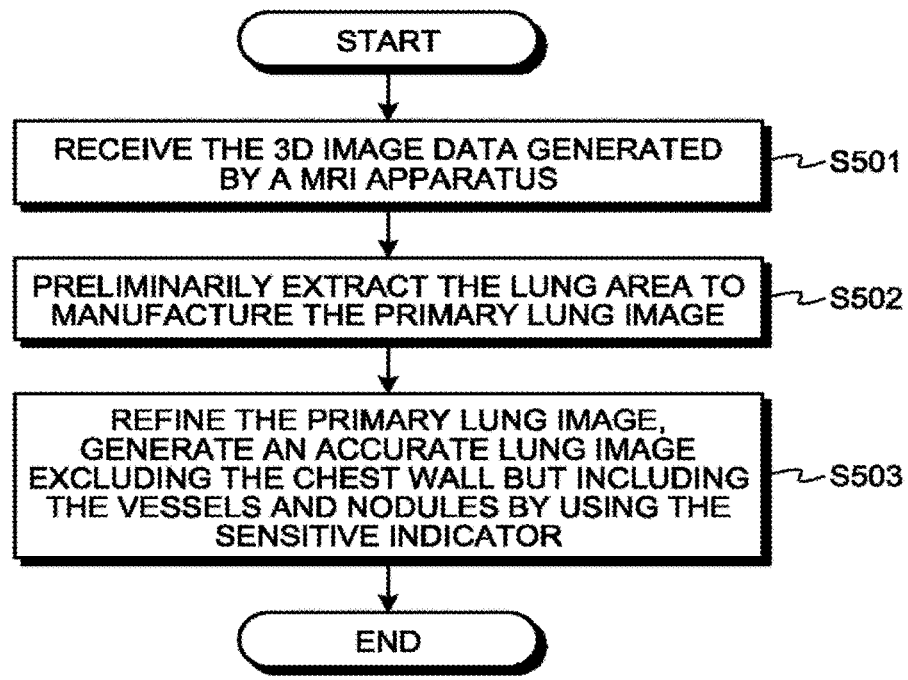
FIG. 5 is a flow chart representing the lung segmentation processing according to the first embodiment of the present invention.

The lung segmentation processing performed by the image processing apparatus 100 is illustrated in combination with FIG. 5 in the follow.

FIG. 5 is a low chart representing lung segmentation processing according to the first embodiment of the present invention. As shown in FIG. 5, first in step S501, after the image processing apparatus 100 receives the 3D image data generated by the MRI apparatus (see FIG. 2), the primary lung image manufacturing part 10 preliminarily extracts the lung area from 3D image data by a rough lung area extraction processing, therefore manufacturing the primary lung image (see FIG. 3) (step S502).

Next, in step S503, the accurate lung image manufacturing part 20 further refines the primary lung image by using the accurate processing model as shown in formula (4), and particularly generates accurate lung image excluding the chest wall but including the vessels and nodules (see FIG. 4) by using the sensitivity indicator contained in the accurate lung image manufacturing part 20.

Furthermore, after accurate lung image manufacturing part 20 completes the above processing, accurate lung image manufacturing part 20 is able to output the generated accurate lung image for facilitating users to read the photographs.

By means of the lung segmentation processing as shown in FIG. 5, the accuracy of the whole lung segmentation of the image generated by MRI apparatus is improved, such that the output lung image could contain no chest wall but completely retain the cavity structure, particularly the relative critical data in the lung diagnosis such as the nodules, so as to be helpful for users to read the photographs.

Embodiment Variant 1

In the first embodiment, the exponential function is used as the gradient sensitivity indicator, and such gradient sensitivity indicator has a more sensitive indicating performance.

However, other gradient sensitivity indicators can also be used as long as the increasing-decreasing relationship between the grey value and g is met. For example, formula (6) can be used as the gradient sensitivity indicator.

$$g = \frac{1}{1 + |\nabla G \otimes I|^2} \quad (6)$$

The sensitivity to gradient can be realized by increasing the power of the Gauss convolution term, for example, by using the function of formula (7) as the gradient sensitivity indicator.

$$g = \frac{1}{1 + |\nabla G \otimes I|^\omega} \quad \omega > 2 \quad (7)$$

Embodiment Variant 2

In the first embodiment, accurate lung image manufacturing part 20 uses the level set distance regularization based accurate processing model. However, other accurate processing models are also applicable, the present invention, can be implemented as long as the gradient sensitivity indicator and the cavity structure sensitivity indicator are contained.

For example, a common level set function model as shown in formula (8) can be used as the accurate processing model, such that the generated accurate lung image excludes the chest walls and includes the cavity structures.

$$\frac{\partial \phi}{\partial t} = \lambda \delta_\varepsilon(\phi)\mathrm{div}\left(g\frac{\nabla \phi}{|\nabla \phi|}\right) + a\delta_\varepsilon(\phi)(g - \mathrm{sign}(k)k) \quad (8)$$

In addition, a model as shown in formula (9) can also be used as the accurate processing model such that the generated accurate lung image excludes the chest walls, wherein, level set distance regularization uses a single-well potential equation only, while the p in formula 4 is replaced with a double-well potential equation.

$$\frac{\partial \phi}{\partial t} = \mu \mathrm{div}\left(\left[\nabla \phi\left(1 - \frac{1}{|\nabla \phi|}\right)\right]\right) + \lambda \delta_\varepsilon(\phi)\mathrm{div}\left(g\frac{\nabla \phi}{|\nabla \phi|}\right) + a\delta_\varepsilon(\phi)(g - \mathrm{sign}(k)k) \quad (9)$$

These embodiment variants can also realize more accurate lung segmentation processing.

Second Embodiment

The second embodiment is based on the first embodiment and differs from the first embodiment in that the image processing apparatus 200 also has a display part 30 in the second embodiment and the accurate lung image manufacturing part 20' in the image processing apparatus 200 has a structure selector 22. The follow primarily illustrates the differences between the first and second embodiments and the repeated explications are appropriately omitted.

Figure 6:
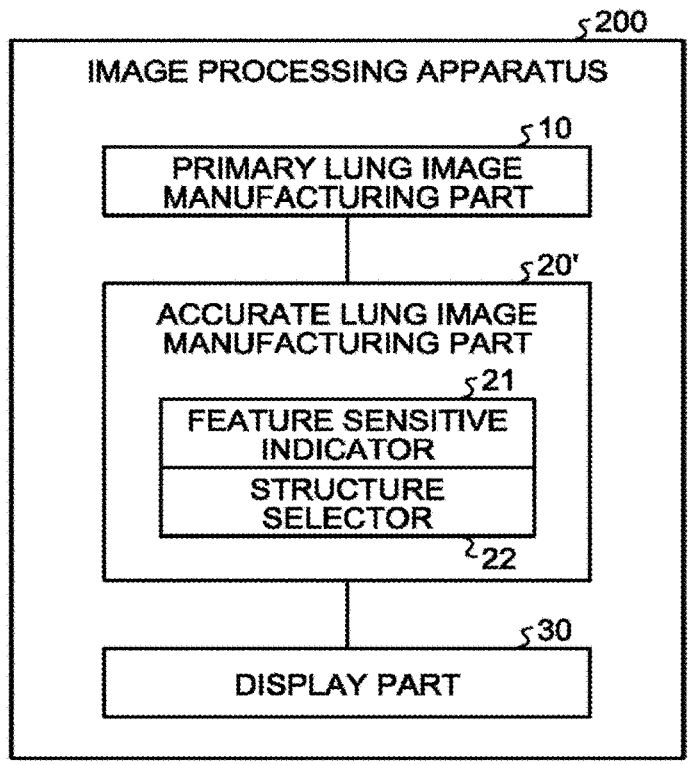
FIG. 6 is a block diagram representing an image processing apparatus according to the second embodiment of the present invention.
Figure 13:
FIG. 13 is an exemplary figure representing the result of lung segmentation processing in the prior art.

FIG. 6 is a block diagram representing an image processing apparatus according to the second embodiment of the present invention. As shown in FIG. 6, the image processing apparatus 200 comprises a primary lung image manufacturing part 10, an accurate lung image manufacturing part 20' and display part 30.

The primary lung image manufacturing part 10 receives the three-dimensional image data of the chest acquired by the MRI apparatus, extracts the lung area from the received image data by rough segmentation methods such as threshold method or binarization segmentation method, so as to manufacture the primary lung image. The primary image manufacturing part 10 may be circuits or software modules which are capable of realizing the above functions.

The accurate lung image manufacturing part 20' further processes the primary lung image, modifying the primary lung image according to the three-dimensional image date of MRI apparatus and thereby manufacturing accurate lung image. The accurate lung image manufacturing part 20' may be circuits or software modules which are capable of realizing said functions.

For example, by using the level set constructed by the pixels of primary lung image as the initial level set, in combination with the original image data information such as the three-dimensional image data of the MRI apparatus, level set evolution segmentation is performed, the accurate lung image is obtained by such iterative algorithm. Such partial differential equation that can reflect the level set evolution and includes the level set function is set as the level set function model.

The display part 30 is used for displaying the processing results of the accurate lung image manufacturing part 20'. The display part 30 may be circuits or software modules which are capable of realizing said function. In addition, it is possible to directly output the processing results of the image processing apparatus 200 and omit the display part 30. In other words, the display part 30 displays lung image data.

The construction of the accurate lung image manufacturing part 20' is illustrated in details as below.

The accurate lung image manufacturing part 20' in the second embodiment comprises a feature sensitivity indicator 21 and a structure selector 22, wherein, the feature sensitivity indicator 21 utilizes the sensitivity to gradient and sensitivity to cavity structure for processing, such that the accurate lung image generated by the accurate lung image manufacturing part 20' excludes the chest walls and include the cavity structures. The feature sensitivity indicator 21 comprises a gradient sensitivity indicator g sensitive to the gradient and a cavity structure sensitivity indicator sign(k)k sensitive to the cavity structure, as illustrated in the first embodiment.

The structure selector 22 performs a selection, such that the cavity structures are selectively excluded from the accurate lung image generated by the accurate lung image manufacturing part 20'.

In particularly, by distinguishing the vessels from the nodules of the cavity structures, structure selector 20 enables the pixels of the vessels or the pixels of the nodules of the original image not to be reflected in the cavity structure sensitivity indicator sign(k)k, so as to select excluding the above-mentioned vessels or nodules from accurate lung image. In other words, the structure selector 22 serving as a generating part receives instructions to select at least one data set of the vessels, the nodules, or tumors, and selectively removes a data set of at least one of the vessels, the nodules, or the tumors from the lung image data.

The structure selector 22 employed in the second embodiment is $1-\beta*W^T D(T_H)$. $\beta$ is a coefficient larger than 0.

The cavity structure model $D(T_H)$ and cavity structure selection matrix W are included in the above-mentioned structure selector 22. The cavity structure module $D(T_H)$ is used for distinguishing the characteristics of different cavity structures so as to realize an easier selection. In cavity structure selection matrix W, the cavity structure which shall be removed could be designated by the setting of different elements in the matrix, so as to complete the selection.

The structure selector 22 enable the cavity structures not to be reflected in the cavity structure indicator sign(k)k by substituting $1-\beta*W^T D(T_H)$ into the accurate processing model, so as to exclude the selected cavity structure from the segmentation results. The following formula (10) shows the level set distance regularization based accurate processing model in the second embodiment.

$$\frac{\partial \phi}{\partial t} = \mu \mathrm{div}(d_p(|\nabla \phi|)\nabla \phi) + \lambda \delta_\varepsilon(\phi)\mathrm{div}\left(g\frac{\nabla \phi}{|\nabla \phi|}\right) + \quad (10)$$
$$a\delta_\varepsilon(\phi)(g - \mathrm{sign}(k)k*(1 - \beta*W^T D(T_H)))$$

In addition, with regard to the cavity structure model $D(T_H)$, H is the Hessian matrix of the original image data representing the inherent features of the image, wherein partial derivative $\partial$ is used. $T_H$ represents three eigenvalues of Hessian matrix $\lambda_1$, $\lambda_2$, $\lambda_3$, and $\lambda_1 \leq \lambda_2 \leq \lambda_3$. The three eigenvectors respectively represent three directions are orthogonal to each other in relative to the area, and reciprocals of eigenvalues corresponding to eigenvectors represent the extension in this direction, the extension in this direction will be greater as the reciprocal of the eigenvalue becoming bigger. There are relationships as illustrated in formula (11) and formula (12):

$$H = \begin{bmatrix} \frac{\partial^2}{\partial_x \partial_x} & \frac{\partial^2}{\partial_x \partial_y} & \frac{\partial^2}{\partial_x \partial_z} \\ \frac{\partial^2}{\partial_y \partial_x} & \frac{\partial^2}{\partial_y \partial_y} & \frac{\partial^2}{\partial_y \partial_z} \\ \frac{\partial^2}{\partial_z \partial_x} & \frac{\partial^2}{\partial_z \partial_y} & \frac{\partial^2}{\partial_z \partial_z} \end{bmatrix} \quad (11)$$

$$T_H = \begin{bmatrix} \lambda_1 \\ \lambda_2 \\ \lambda_3 \end{bmatrix}, \quad D(T_H) = \begin{bmatrix} \lambda'_1 \\ \lambda'_2 \\ \lambda'_3 \end{bmatrix} = \begin{bmatrix} |\lambda_1| \\ |\lambda_2|*e^{-n*\lambda_1^2} \\ |\lambda_3|*e^{-n*\lambda_2^2} \end{bmatrix} \quad (12)$$

wherein n is a coefficient set arbitrarily as needed. The cavity structures can be distinguished by different combination of $\lambda'_1$, $\lambda'_2$ and $\lambda'_3$. The combinations to which different cavity structures correspond are shown in the following table 1.

TABLE 1

| | $D(T_H)$ | | |
|---|---|---|---|
| | $\lambda'_1$ | $\lambda'_2$ | $\lambda'_3$ |
| plane | L | L | H |
| tubular (vessels) | L | H | L |
| spherical (nodules) | H | L | L | wherein, in the table 1, H=High, L=Low≈0.

As such, different cavity structures can be distinguished by using Hessian matrix of original image.

In addition, the cavity structure selection matrix W refers to a value which is multiplied by the cavity structure model $D(T_H)$ to select different cavity structures represented by cavity structure model $D(T_H)$. Different cavity structures can be selected by defining W as different values.

For example, in case of defining the values of matrix W with "0" and "1", the value of W may be $$\begin{bmatrix}0\\0\\0\end{bmatrix} \text{ or } \begin{bmatrix}0\\1\\0\end{bmatrix} \text{ or } \begin{bmatrix}1\\0\\0\end{bmatrix} \text{ or } \begin{bmatrix}1\\1\\0\end{bmatrix}.$$

If the whole lung image is adopted without any exclusion, W is $$\begin{bmatrix}0\\0\\0\end{bmatrix}.$$

If vessels are excluded and nodules are retained, W is $$\begin{bmatrix}0\\1\\0\end{bmatrix}.$$

If nodules are excludes and vessels are retained, W is $$\begin{bmatrix}1\\0\\0\end{bmatrix};$$

If both the nodules and vessels are excluded, W is $$\begin{bmatrix}1\\1\\0\end{bmatrix}.$$

For example, in case of $$D(T_H) = \begin{bmatrix}L\\H\\L\end{bmatrix},$$

if vessels are desired to be excluded, as long as setting W as $$\begin{bmatrix}0\\1\\0\end{bmatrix},$$

then $$W^T D(T_H) = \begin{bmatrix}0\\1\\0\end{bmatrix}^T \begin{bmatrix}L\\H\\L\end{bmatrix} = H,$$

and thereby $1-\beta*W^T D(T_H)=L$.

FIG. 8 shows an exemplary figure of the results of the lung segmentation processing when the vessels are desired to be excluded. As shown in FIG. 8, there is no data of chest wall tissue left in the edge area pointed by arrow A. In addition, under the combined action of the cavity structure sensitivity indicator and the structure selector 22, the vascular tissue pointed by arrow B is completely excluded and the nodule pointed by arrow C is retained.

In the second embodiment, the primary lung image manufacturing part 10 corresponds to "primary lung image manufacturing mechanism", the accurate lung image manufacturing part 20' corresponds to "accurate lung image manufacturing mechanism", the feature sensitivity indicator 21 corresponds to "feature sensitivity indicating unit", the structure selector 22 corresponds to "selecting unit", and display part 30 corresponds to "display mechanism".

In the following, for example in the case that the accurate lung image shown in FIG. 8 is required to be obtained, the procedure of the lung segmentation processing performed by the image processing apparatus 200 is illustrated in combination with FIG. 7.

FIG 7 is a flow chart representing the lung segmentation processing according to the second embodiment of the present invention. As shown in FIG. 7, first in step S701, after the image processing apparatus 200 receives the 3D image data generated by MRI apparatus (see FIG. 2), the primary lung image manufacturing part 10 preliminarily extracts the lung area from 3D image data by a rough lung area extraction processing, therefore manufacturing a primary lung image (see FIG. 3) (step S702).

Next, in step S703, the accurate lung image manufacturing part 20' further refines the primary lung image by using the accurate processing model of formula (10), selects the vessels as the cavity structures to be excluded by using the sensitivity indicator and structure selector, in particular using the cavity structure sensitivity indicator and structure selector simultaneously, so as to generate an accurate lung image excluding chest wall and vessels but including nodules.

Next, in step S704, display part 30 displays the generated accurate lung image as shown in FIG. 8.

The accuracy of the whole lung segmentation of the image generated by a MRI apparatus is improved by the lung segmentation processing as shown in FIG. 7. By enabling the pixel of vessels or the pixel of nodules not to be reflected in the sensitivity to cavity structure, the segmentation result excluding vessels but including nodules could be selected, thereby the vessels and nodules can be distinguished better so as to be processed respectively. Because of the optional and more reliable vessel excluding, it is optional for the users whether or not to exclude the vessels, and the vessels could be excluded while the nodules are retained, therefore the efficiency in reading photographs is improved.

There are many other selections in addition to the selection as shown in FIG. 8. For example, FIG. 9 is an exemplary figure representing different processing results generated based on different selection of structure selector when process the image data of MRI apparatus, wherein picture (1) in FIG. 9 represents the situation that the whole lung is segmented out, namely all cavity structures are included, picture (2) in FIG. 9 represents the situation that the vessels are excluded and nodules included, and picture (3) in FIG. 9 represents the situation that the nodules are excluded and vessels included.

In addition, FIG. 10 is another exemplary figure representing different processing results generated based on different selection of structure selector when process the image data of MRI apparatus, wherein picture (1) in FIG. 10 represents the situation that the whole lung is segmented out, namely all cavity structures are included, picture (2) in FIG. 10 represents the situation that the vessels are excluded and nodules included, and picture (3) in FIG. 10 represents the situation that the nodules are excluded and vessels included.

Embodiment Variant 1

In the second embodiment, it is feasible that accurate lung image manufacturing part 20' comprises a selection change accepting and handling unit, this selection change accepting and handling unit accepts and handles the change for the selection performed by the structure selector 22.

That is to say, the selection change accepting and handling unit can change the types of the cavity structures reflected in the sensitivity to cavity structure by changing the value of W, so as to be able to change the types of the accurate lung images displayed on the display part 30. In other words, the second image manufacturing part 20' serving as a generating part further receives instructions to make further change in the instructed selection of at least one data set of the vessels, nodules, or tumors, and makes change in the instructed selection of at least one data set of the vessels, the nodules, or the tumors to be removed from the lung image data.

Thus, the users can change the types of the accurate lung segmentation results to be displayed at any time.

Embodiment Variant 2

The embodiment variant of the first embodiment is also applicable to the second embodiment. For example, the normal level set function model of formula (13) can be used as an accurate processing model. In other words, the second image manufacturing part 20 serving as a generating part uses a common level set function model to manufacture lung image data.

$$\frac{\partial \phi}{\partial t} = \lambda \delta_\varepsilon(\phi) \mathrm{div}\left(g \frac{\nabla \phi}{|\nabla \phi|}\right) + a\delta_\varepsilon(\phi)(g - \mathrm{sign}(k)k * (1 - \beta * W^T D(T_H))) \quad (13)$$

In addition, a model as shown in formula (14) can also be used as accurate processing model wherein, level set distance regularization uses a single-well potential equation only, while the p in formula 10 is replaced with a double-well potentional equation.

$$\frac{\partial \phi}{\partial t} = \mu \mathrm{div}\left(\left[\nabla \phi\left(1 - \frac{1}{|\nabla \phi|}\right)\right]\right) + \lambda \delta_\varepsilon(\phi) \mathrm{div}\left(g \frac{\nabla \phi}{|\nabla \phi|}\right) + \\ a\delta_\varepsilon(\phi)(g - \mathrm{sign}(k)k * (1 - \beta * W^T D(T_H))) \quad (14)$$

These embodiment variants can also accomplish more accurate lung segmentation processing.

Embodiment Variant 3

In the first and second embodiments, three dimensional image of MRI apparatus is employed as the subject to be processed, however the present Invention can also process the image acquired by CT apparatus.

FIG. 11 is an exemplary FIG. representing different processing results generated based on different selections of the structure selector when process the image data of CT apparatus, wherein picture (1) in FIG. 11 represents the situation that the whole lung is segmented out, namely all cavity structures are included, picture (2 ) in FIG. 11 represents the situation that the vessels are excluded and nodules included, and picture (3) in FIG. 11 represents the situations that the nodules are excluded and vessels included.

FIG. 12 is another exemplary figure representing different processing results generated based on different selections of the structure selector when process the image data of CT apparatus, wherein picture (1) in FIG. 12 represents the situation that the whole lung is segmented out, namely all cavity structures are included, picture (2) in FIG. 12 represents the situation that the vessels are excluded and nodules included, and picture (3) in FIG. 12 represents the situation that the nodules are excluded and vessels included.

Embodiment Variant 4

In the present invention, the size of the weighted area is changed by changing and impacting the strength of expansion or contraction during the level set evolution, the sensitivity indicator for the cavity structures is added, and the purpose of making the structures as a result selectable is achieved by using the structure unit. The specific models used in the present invention can be changed arbitrarily as long as the inventive conception of the present invention can be achieved.

In addition, the coefficients in the above formulas can be selected according to the requirements for the images and the environments. For example, in the case of compressing the image region between 0-255, the following parameters are preferably adopted: $\mu=0.001$, $\lambda=5.0$, $\varepsilon=1.55$, $\alpha=-6.0$, $\beta=1.0$, $\gamma=-0.5$, $m=0.5$, $n=1.0$.

Moreover, during the evolution, the number of iterations is 80 and step length t is 10.0. Various parameters can be adjusted according to the corresponding situation, and the region is not explicit limited and is adjusted according to the actual effects, but the parameters constraints $\mu$, $\lambda$, $\varepsilon$, $\beta$, $m$, $n>0$, and $\alpha$, $\gamma<0$ need to be met.

Embodiment Variant 5

In the above embodiments, three dimensional images are adopted for illustration, though the present invention is also applicable to images of other dimensions through deductions. For example, in case of using for 2D images, the structure selector may be different since only tubular and spherical structures need to be considered for 2D images, the Hessian matrix and other corresponding formulas change as shown in FIGS. (15) and (16).

$$H = \begin{bmatrix} \frac{\partial^2}{\partial_x \partial_x} & \frac{\partial^2}{\partial_x \partial_y} \\ \frac{\partial^2}{\partial_y \partial_x} & \frac{\partial^2}{\partial_y \partial_y} \end{bmatrix} \quad (15)$$

$$T_H = \begin{bmatrix} \lambda_1 \\ \lambda_2 \end{bmatrix}, \quad D(T_H) = \begin{bmatrix} \lambda_1' \\ \lambda_2' \end{bmatrix} = \begin{bmatrix} |\lambda_1| \\ |\lambda_2| * e^{-n*\lambda_1^2} \end{bmatrix} \quad (16)$$

Accordingly, the range of value of W is $$\begin{bmatrix} 0 \\ 0 \end{bmatrix} \text{ or } \begin{bmatrix} 1 \\ 0 \end{bmatrix} \text{ or } \begin{bmatrix} 0 \\ 1 \end{bmatrix} \text{ or } \begin{bmatrix} 1 \\ 1 \end{bmatrix}.$$

The image processing apparatus of the present invention may be a processing apparatus containing a processor and a memory, wherein the memory stores the instruction information corresponding tithe actions of manufacturing part and the first and second processing parts as illustrated in the above embodiments, and the processor implements the invention by reading and executing the instruction information in the memory.

Figure 14:
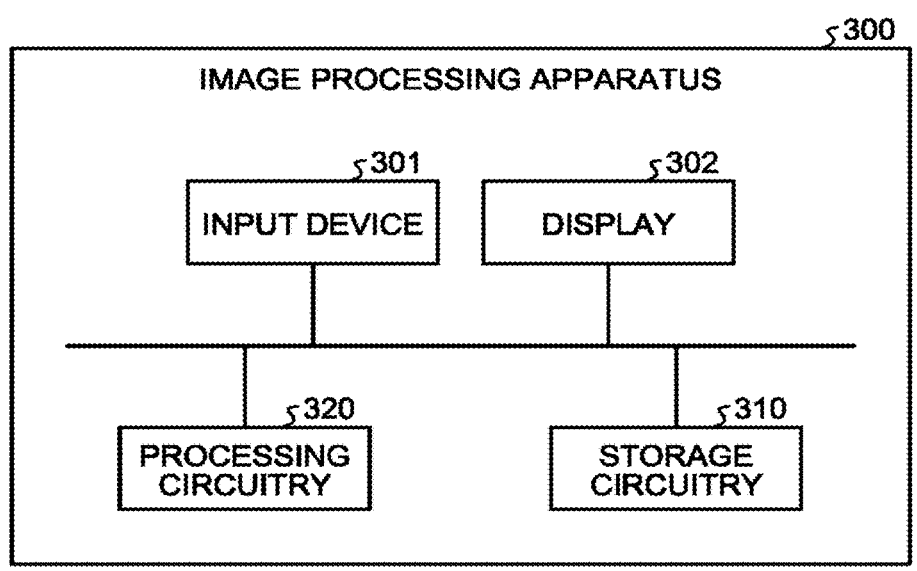
FIG. 14 is a block diagram representing a configuration example of an image processing apparatus according to the present invention.

FIG. 14 is a block diagram representing a configuration example of an image processing apparatus according to the present invention. An image processing apparatus 300 can be, for example, a general-purpose apparatus such as a personal computer and a tablet computer. The image processing apparatus 300 includes an input unit 301, a display 302, storage circuitry 310, and processing circuitry 320. The input unit 301, the display 302, the memory circuitry 310, and the processing circuitry 320 can be communicatively connected.

The input unit 301 is a unit such as a mouse, a keyboard, a touch panel for receiving various instructions and configuration requests from an operator. The display 302 is a unit for displaying medical images, and displaying GUI for allowing the operator to input various configuration requests by using the input unit 301.

The storage circuitry 310 can be, for example, a NAND (Not AND) flash memory or an HDD (Hard Disk Drive) which stores various programs for displaying medical image data and GUI, and stores information to be used by the programs.

The processing circuitry 320 is an electronic device (processor) for controlling the entire process in the image processing apparatus 300. The processing circuitry 320 performs processes corresponding to the feature sensitivity indicator 21 and the second image manufacturing part 20. The processing circuitry 320 may also perform a process corresponding to the first image manufacturing part 10, the structure selector 22 or the display part 30.

The image processing apparatus of the present invention can also be installed on the medical device as circuits capable of implementing the functions illustrated in various embodiments, and may also be provided as programs executable by the computer, stored in the storage mediums such as disks (soft disk (floppy, registered trademark), hard disk, etc.), compact discs (CD-ROM, DVD, etc.), photomagneto disks (MO) and semiconductor memory.

In addition, the MW (Middleware) such as OS (Operation System), database management software and network software, running on a computer based on the instructions of the programs installed from the storage mediums to the computer, can also perform a portion of the processing for implementing the above embodiments.

Though several embodiments of this invention are illustrated above, these embodiments are proposed as examples, and are not intended to limit the scope of the invention. These new embodiments may be implemented in any other forms, various omissions, substitutions and changes could be made without departing from the spirit of the invention. These embodiments or variants thereof are within the scope or in conformity with the spirit of the invention, as well as fall in the scope of the invention recorded in claims and equivalent thereof.

What is claimed is:

1. An image processing apparatus comprising:
processing circuitry configured to
recognize at least one of a chest wall, vessels, nodules, and tumors by increasing a sensitivity to a gradient and a sensitivity to a cavity structure in three-dimensional data including a lung area,
generate lung image data corresponding to the lung area by performing a data removing process for removing data derived from the chest wall and a data holding process for holding data derived from at least one of the vessels, the nodules, and the tumors based on a result obtained by the recognizing, and
output the lung image data.

2. The image processing apparatus according to claim 1, wherein the processing circuitry is further configured to generate pre-processed lung image data which is obtained by extracting the lung area from the three-dimensional image data through pre-processing different from the data removing process and the data holding process, and perform the data removing process and the data holding process on the pre-processed lung image data, thereby generating the lung image data.

3. The image processing apparatus according to claim 1, wherein the processing circuitry is further configured to recognize the data derived from the chest wall by using, as the sensitivity to the gradient, a function including a grey value as an exponent.

4. The image processing apparatus according to claim 1, wherein the processing circuitry is further configured to recognize the data derived from at least one of the vessels, the nodules, and the tumors by using, as the sensitivity to the cavity structure, a binarization of a curvature value obtained by comparison with a threshold.

5. The image processing apparatus according to claim 1, wherein the processing circuitry is further configured to allow multiplying level set distance regularization by a value obtained through subtraction of the sensitivity to the cavity structure from the sensitivity to the gradient, thereby the cavity structure is included in the lung image data.

6. The image processing apparatus according to claim 1, wherein the processing circuitry is further configured to receive instructions to select at least one data set of the vessels, the nodules, and the tumors, and selectively remove a data set of at least one of the vessels, the nodules, and the tumors from the lung image data.

7. The image processing apparatus according to claim 6, wherein the processing circuitry is further configured to receive instructions to make a change in the instructed selection of at least one data set of the vessels, the nodules, and the tumors, and make the change in the instructed selection of at least one data set of the vessels, the nodules, and the tumors to be removed from the lung image data.

8. The image processing apparatus according to claim 1, wherein the processing circuitry is further configured to use a common level set function model to generate the lung image data.

9. The image processing apparatus according to claim 1, wherein the three-dimensional image data is magnetic resonance imaging image data acquired by an magnetic resonance imaging apparatus.

10. An magnetic resonance imaging apparatus, comprising:
processing circuitry configured to
recognize at least one of a chest wall, vessels, nodules, and tumors by increasing a sensitivity to a gradient and a sensitivity to a cavity structure in three-dimensional data including a lung area,
generate lung image data corresponding to the lung area by performing a data removing process for removing data derived from the chest wall and a data holding process for holding data derived from at least one of the vessels, the nodules, and the tumors based on a result obtained by the recognizing, and output the lung image data.

11. An image processing method, comprising:

recognizing at least one of a chest wall, vessels, nodules, and tumors by increasing a sensitivity to a gradient and a sensitivity to a cavity structure in three-dimensional data including a lung area, generating lung image data corresponding to the lung area by performing a data removing process for removing data derived from the chest wall and a data holding process for holding data derived from at least one of the vessels, the nodules, and the tumors based on a result obtained by the recognizing, and outputting the lung image data.

* * * * *